(12) United States Patent
Swayze et al.

(10) Patent No.: US 10,206,686 B2
(45) Date of Patent: Feb. 19, 2019

(54) BRONCHUS SEALANTS AND METHODS OF SEALING BRONCHIAL TUBES

(71) Applicant: Ethicon Endo-Surgery, Inc., Cincinnati, OH (US)

(72) Inventors: Jeffrey S. Swayze, Hamilton, OH (US); Anne J. Gorman, Highstown, NJ (US); Jason L. Harris, Lebanon, OH (US); Frederick E. Shelton, IV, Hillsboro, OH (US)

(73) Assignee: Ethicon LLC, Guaynabo, PR (US)

( * ) Notice: Subject to any disclaimer, the term of this patent is extended or adjusted under 35 U.S.C. 154(b) by 670 days.

(21) Appl. No.: 14/300,819

(22) Filed: Jun. 10, 2014

(65) Prior Publication Data
US 2015/0351776 A1 Dec. 10, 2015

(51) Int. Cl.
*A61B 17/12* (2006.01)
*A61B 17/00* (2006.01)
(Continued)

(52) U.S. Cl.
CPC .... *A61B 17/12177* (2013.01); *A61B 1/00082* (2013.01); *A61B 1/00087* (2013.01); *A61B 1/00101* (2013.01); *A61B 1/00137* (2013.01); *A61B 1/018* (2013.01); *A61B 1/126* (2013.01); *A61B 1/2676* (2013.01); *A61B 17/00234* (2013.01); *A61B 17/00491* (2013.01); *A61B 17/064* (2013.01); *A61B 17/07207* (2013.01);
(Continued)

(58) Field of Classification Search
None
See application file for complete search history.

(56) References Cited

U.S. PATENT DOCUMENTS 5,503,638 A * 4/1996 Cooper ............ A61B 17/07207
606/148
5,698,213 A 12/1997 Jamiolkowski et al.
(Continued)

FOREIGN PATENT DOCUMENTS

WO WO-01/02042 A1 1/2001
WO WO-02/22072 A2 3/2002
(Continued)

OTHER PUBLICATIONS

Chen et al. "Elastomeric Biomaterials for Tissue Engineering." Prog. Polymer. Sci. 38(2013):584-671.
(Continued)

*Primary Examiner* — Shaun David
(74) *Attorney, Agent, or Firm* — Mintz, Levin, Cohn, Ferris, Glovsky and Popeo, P.C.

(57) ABSTRACT

Bronchus sealants and methods of sealing bronchial tubes are provided. In general, the bronchus sealants and methods of sealing bronchial tubes can facilitate sealing of stapled bronchial tubes. In some embodiments, a reinforcement material can be introduced into a bronchial tube, and then the bronchial tube and the reinforcement material can be stapled using a surgical stapler. A sealant can be introduced into the bronchial tube and can harden therein, thereby helping to seal the bronchial tube where the bronchial tube was stapled. The sealant can be introduced into the bronchial tube before and/or after the stapling of the bronchial tube and the reinforcement material.

20 Claims, 7 Drawing Sheets

(51) Int. Cl.
    *A61B 1/267* (2006.01)
    *A61B 17/064* (2006.01)
    *A61B 1/018* (2006.01)
    *A61B 19/00* (2006.01)
    *A61B 90/30* (2016.01)
    *A61B 17/072* (2006.01)
    *A61B 1/00* (2006.01)
    *A61B 1/12* (2006.01)
    *A61B 34/20* (2016.01)

(52) U.S. Cl.
    CPC .. *A61B 17/07292* (2013.01); *A61B 17/12104* (2013.01); *A61B 17/12136* (2013.01); *A61B 17/12181* (2013.01); *A61B 17/12186* (2013.01); *A61B 19/5202* (2013.01); *A61B 90/30* (2016.02); *A61B 2017/0023* (2013.01); *A61B 2017/00115* (2013.01); *A61B 2017/00296* (2013.01); *A61B 2017/00495* (2013.01); *A61B 2017/00809* (2013.01); *A61B 2017/00876* (2013.01); *A61B 2034/2051* (2016.02); *A61B 2090/309* (2016.02)

(56) References Cited

U.S. PATENT DOCUMENTS

| | | | |
|---|---|---|---|
| 5,700,583 A | 12/1997 | Jamiolkowski et al. | |
| 5,895,412 A * | 4/1999 | Tucker | A61B 17/00491 606/213 |
| 6,183,498 B1 * | 2/2001 | Devore | A61B 17/00491 530/356 |
| 6,328,689 B1 * | 12/2001 | Gonzalez | A61B 17/00234 600/37 |
| 6,527,761 B1 * | 3/2003 | Soltesz | A61B 17/12022 604/509 |
| 7,143,924 B2 | 12/2006 | Scirica et al. | |
| 7,143,925 B2 | 12/2006 | Shelton, IV et al. | |
| 7,757,692 B2 * | 7/2010 | Alferness | A61B 17/12022 128/207.15 |
| 7,772,352 B2 | 8/2010 | Bezwada | |
| 8,317,070 B2 | 11/2012 | Hueil et al. | |
| 8,393,514 B2 | 3/2013 | Shelton, IV et al. | |
| 8,551,058 B2 | 10/2013 | Measamer et al. | |
| 2002/0147462 A1 * | 10/2002 | Mair | A61B 17/12022 606/213 |
| 2003/0036755 A1 * | 2/2003 | Ginn | A61B 17/0644 606/41 |
| 2003/0181922 A1 * | 9/2003 | Alferness | A61B 17/12022 606/108 |
| 2005/0069589 A1 | 3/2005 | Lowinger et al. | |
| 2005/0137714 A1 * | 6/2005 | Gonzalez | A61B 17/12022 623/23.65 |
| 2005/0281801 A1 * | 12/2005 | Gong | A61K 47/48276 424/94.3 |
| 2006/0257458 A1 | 11/2006 | Gorman et al. | |
| 2008/0283065 A1 * | 11/2008 | Chang | A61M 16/0406 128/898 |
| 2009/0136589 A1 * | 5/2009 | Crabtree | A61L 24/02 424/602 |
| 2009/0205643 A1 | 8/2009 | Tanaka et al. | |
| 2009/0234193 A1 | 9/2009 | Weisenburgh, II et al. | |
| 2009/0270686 A1 | 10/2009 | Duke et al. | |
| 2010/0114126 A1 * | 5/2010 | Neff | A61B 17/52 606/151 |
| 2011/0192882 A1 | 8/2011 | Hess et al. | |
| 2012/0024934 A1 | 2/2012 | Shelton, IV et al. | |
| 2012/0080335 A1 | 4/2012 | Shelton, IV et al. | |
| 2012/0083835 A1 | 4/2012 | Shelton, IV et al. | |
| 2012/0289776 A1 * | 11/2012 | Keast | A61B 17/221 600/106 |
| 2012/0292369 A1 | 11/2012 | Munro, III et al. | |
| 2013/0112733 A1 | 5/2013 | Aranyi et al. | |
| 2013/0146642 A1 | 6/2013 | Shelton, IV et al. | |
| 2013/0153641 A1 | 6/2013 | Shelton, IV et al. | |
| 2013/0161374 A1 | 6/2013 | Swayze et al. | |
| 2013/0256365 A1 | 10/2013 | Shelton, IV et al. | |
| 2013/0256372 A1 | 10/2013 | Baxter, III et al. | |
| 2013/0256376 A1 | 10/2013 | Barton et al. | |
| 2013/0256377 A1 | 10/2013 | Schmid et al. | |
| 2014/0158741 A1 | 6/2014 | Woodard, Jr. et al. | |
| 2014/0271472 A1 * | 9/2014 | Patel | A61K 35/38 424/1.85 |
| 2015/0173756 A1 | 6/2015 | Baxter et al. | |
| 2015/0272575 A1 | 10/2015 | Leimbach et al. | |

FOREIGN PATENT DOCUMENTS

| | | |
|---|---|---|
| WO | WO-2007014313 A2 | 2/2007 |
| WO | 14016819 A1 | 1/2014 |

OTHER PUBLICATIONS

Lim et al. "Fabrication and Evaluation of Poly(epsilon-caprolactone)/Silk Fibroin Blend Nanofibrous Scaffold." Biopolymers.97(2012):265-275.
U.S. Appl. No. 13/763,192, filed Feb. 8, 2013.
U.S. Appl. No. 14/074,810, filed Nov. 8, 2013.
U.S. Appl. No. 14/074,884, filed Nov. 8, 2013.
U.S. Appl. No. 14/074,902, filed Nov. 8, 2013.
U.S. Appl. No. 14/075,438, filed Nov. 8, 2013.
U.S. Appl. No. 14/075,459, filed Nov. 8, 2013.
U.S. Appl. No. 14/300,793, filed Jun. 10, 2014.
U.S. Appl. No. 14/300,799, filed Jun. 10, 2014.
U.S. Appl. No. 14/300,801, filed Jun. 10, 2014.
U.S. Appl. No. 14/300,804, filed Jun. 10, 2014.
U.S. Appl. No. 14/300,807, filed Jun. 10, 2014.
U.S. Appl. No. 14/300,811, filed Jun. 10, 2014.
U.S. Appl. No. 14/300,815, filed Jun. 10, 2014.
U.S. Appl. No. 14/300,817, filed Jun. 10, 2014.
U.S. Appl. No. 14/300,820, filed Jun. 10, 2014.
U.S. Appl. No. 14/300,954, filed Jun. 10, 2014.
Zhao et al. "Biodegradable Fibrous Scaffolds Composed of Gelatin Coated Poly(?-caprolactone) Prepared by Coaxial Elecrospinning." J. Biomed. Mater. Res. 83A(2007):372-382.
Extended European Search Report dated Aug. 11, 2015, in European Application No. 15171465 (7 Pages).
International Search Report and Written Opinion for Application No. PCT/US2015/030680 dated Jun. 25, 2015.

* cited by examiner

BRONCHUS SEALANTS AND METHODS OF SEALING BRONCHIAL TUBES

FIELD

The subject matter disclosed herein relates to bronchus sealants and methods of sealing bronchial tubes.

BACKGROUND

Surgical staplers are used in surgical procedures to seal, divide, and/or transect tissues in the body by closing openings in tissue, blood vessels, ducts, shunts, or other objects or body parts involved in the particular procedure. The openings can be naturally occurring, such as passageways in blood vessels, airways or an internal lumen or organ like the stomach, or they can be formed by the surgeon during a surgical procedure, such as by puncturing tissue or blood vessels to form a bypass or an anastomosis, or by cutting tissue during a stapling procedure.

Most staplers have a handle with an elongate flexible or rigid shaft having a pair of opposed jaws formed on an end thereof for holding and forming staples therebetween. At least one of the opposed jaws is movable relative to the other jaw. In the case of laparoscopic surgery, often one jaw is fixed and the other is movable. In some devices (for example an open linear stapler), the opposed jaws can be separated by the operator and reassembled providing the relative motion needed for tissue placement. The staples are typically contained in a staple cartridge, which can house multiple rows of staples and is often disposed in one of the two jaws for ejection of the staples to the surgical site. In use, the jaws are positioned so that the object to be stapled is disposed between the jaws, and staples are ejected and formed when the jaws are closed and the device is actuated. Some staplers include a knife configured to travel between rows of staples in the staple cartridge to longitudinally cut the stapled tissue between the stapled rows. Placement of the device, manipulation of components or systems of the device, and other actuations of the device such as articulation, firing, etc. can be accomplished in a variety of ways, such as electromechanically, mechanically, or hydraulically.

In the particular case of stapling bronchial tubes, such as during lung resection, it is important for no leaks to be present after stapling so that air does not inappropriately enter or exit the lung and/or the thoracic cavity. Air escaping a stapled bronchial tube through a leak can interfere with breathing and lung function, such as by preventing full intake of air. Air exiting a stapled bronchial tube into the thoracic cavity through a leak is unsterile and can cause infection and/or other complications in the otherwise sterile environment of the thoracic cavity. However, it can be difficult to prevent leaks in bronchial tubes for a variety of reasons. The small size of bronchial tubes can make delivery of any sealing materials into bronchial tubes difficult, inflammation due to implanted staples and/or other objects and materials can cause bronchial tubes to close or nearly close since they have small diameters, and/or it can be difficult for sealing materials introduced into a bronchial tube to withstand the repeated expansion and contraction of the lung without failing and/or moving within the tube so as to break the seal of the bronchial tube.

Accordingly, there remains a need for improved bronchus sealants and methods of sealing bronchial tubes.

SUMMARY

A surgical method is provided that in one embodiment includes transorally advancing a reinforcement material into a bronchial tube, and introducing a sealant into the bronchial tube and applying the sealant to the reinforcement material within the bronchial tube. The sealant can transition from a first state to a second, harder state within the bronchial tube so as to secure the reinforcement material in a fixed position relative to the bronchial tube.

The method can vary in any number of ways. For example, advancing the reinforcement material can includes advancing a distal end of a scoping device into the bronchial tube and introducing the reinforcement material into the bronchial tube through the scoping device. Introducing the sealant can include introducing the sealant into the bronchial tube through the scoping device with the sealant in the first state. For another example, the method can include stapling the bronchial tube and the reinforcement material that has been introduced into the bronchial tube. The sealant can be introduced and applied before the stapling of the bronchial tube and the reinforcement material, or the sealant can be introduced and applied after the stapling of the bronchial tube and the reinforcement material. A first component of the sealant can be introduced and applied before the stapling of the bronchial tube and the reinforcement material, and a second component of the sealant can be introduced and applied after the stapling of the bronchial tube and the reinforcement material.

In another embodiment, a surgical method is provided that includes positioning a reinforcement material within a bronchial tube, stapling the bronchial tube and the reinforcement material so as to form a staple line extending across the bronchial tube, and applying a sealant to the reinforcement material within the bronchial tube. The sealant can move from a first state to a second, more rigid state within the bronchial tube so as to facilitate sealing of the staple line.

The method can have any number of variations. For example, the method can include expanding an inner diameter of the bronchial tube with a balloon while at least one of the reinforcement material is being positioned and the sealant is being applied. For another example, the method can include, after positioning the reinforcement material and prior to the stapling, locating the reinforcement material within the bronchial tube by illuminating a light. For still another example, the reinforcement material can include at least one of a mesh, a non-woven matrix, a film, a melt-blown non-woven material, a felt material, a closed-cell foam, an open-cell foam, a sponge, a braided suture, poliglecaprone, polyglactin, polydioxanone, collagen, oxidized regenerated cellulose, regenerated cellulose, glycerol, glycolide, lactide, dioxanone, trimethylene carbonate, gut suture, polypropylene, polyethylene, polybutester fiber, stainless steel, nylon, polyester, silk, polyvinylidene difluoride, oxidized cellulose, and polypropylene. For another example, the sealant can include at least one of an adhesive, fibrin thrombin, a hydrogel, fibronectin, gelatin, collagen, Factor XIII, transglutaminase, Polyethylene glycol, alginate, carboxymethylcellulose, methylcellulose, hydroxypropylmethyl cellulose, pectin, polyvinyl alcohol, polyvinylpyrrolidone, benzocaine, cyanoacrylate, polyglycolic acid, hyaluronic acid, magnesium peroxide, 2-octyl cyanoacrylate, and hydrogen peroxide. For yet another example, the method can include, after positioning the reinforcement material and prior to the stapling, locating the reinforcement material within the bronchial tube by positioning a magnet outside the bronchial tube. The magnet can magnetically engage a target located within the bronchial tube adjacent to the reinforcement material. Positioning the reinforcement material can include introducing the reinforcement material into the bronchial tube using a delivery device, the target being attached to a distal end of the delivery device. The target can include one of a Hall sensor and a second magnet.

In another embodiment, a surgical method is provided that includes positioning a reinforcement material within a bronchial tube, and stapling the bronchial tube and the reinforcement material so as to form a staple line extending across the bronchial tube with the reinforcement material engaged within the staple line. An actuator coupled to the reinforcement material can move from a first state to a second, harder state after the stapling so as to facilitate sealing of the staple line.

The method can vary in any number of ways. For example, the method can include, after positioning the reinforcement material and prior to the stapling, locating the reinforcement material within the bronchial tube by illuminating a light inside the bronchial tube. For another example, the reinforcement material can include at least one of a mesh, a non-woven matrix, a film, a melt-blown non-woven material, a felt material, a closed-cell foam, an open-cell foam, a sponge, a braided suture, poliglecaprone, polyglactin, polydioxanone, collagen, oxidized regenerated cellulose, regenerated cellulose, glycerol, glycolide, lactide, dioxanone, trimethylene carbonate, gut suture, polypropylene, polyethylene, polybutester fiber, stainless steel, nylon, polyester, silk, polyvinylidene difluoride, and polypropylene. For yet another example, the actuator can include a biologic foam. For another example, the method can include, after positioning the reinforcement material and prior to the stapling, locating the reinforcement material within the bronchial tube by positioning a magnet outside the bronchial tube. The magnet can magnetically engage a target located within the bronchial tube adjacent to the reinforcement material.

BRIEF DESCRIPTION OF THE DRAWINGS

The invention will be more fully understood from the following detailed description taken in conjunction with the accompanying drawings, in which.

DETAILED DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of such devices and methods is defined solely by the claims. The features illustrated or described in connection with one exemplary embodiment may be combined with the features of other embodiments. Such modifications and variations are intended to be included within the scope of the devices and methods described herein. Further, in the present disclosure, like-numbered components of the various embodiments generally have similar features when those components are of a similar nature and/or serve a similar purpose.

Reference throughout the specification to "various embodiments," "some embodiments," "one embodiment," or "an embodiment," or the like, means that a particular feature, structure, or characteristic described in connection with the embodiment is included in at least one embodiment.

Thus, appearances of the phrases "in various embodiments," "in some embodiments," "in one embodiment," or "in an embodiment," or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation. Such modifications and variations are intended to be included within the scope of the methods, apparatus, devices, and systems described herein.

Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

The terms "proximal" and "distal" are used herein with reference to a clinician manipulating the handle portion of the surgical instrument. The term "proximal" referring to the portion closest to the clinician and the term "distal" referring to the portion located away from the clinician. It will be further appreciated that, for convenience and clarity, spatial terms such as "vertical," "horizontal," "up," and "down" may be used herein with respect to the drawings. However, surgical instruments are used in many orientations and positions, and these terms are not intended to be limiting and/or absolute.

Various exemplary bronchus sealants and methods of sealing bronchial tubes are provided. In general, the bronchus sealants and methods of sealing bronchial tubes can facilitate sealing of stapled bronchial tubes. In some embodiments, a reinforcement material, e.g., a mesh (e.g., a knitted mesh, a non-woven mesh, or a woven mesh), a non-woven matrix, a film, a melt-blown non-woven material, a felt material, a closed-cell foam, an open-cell foam, a braided suture, or a sponge, can be introduced into a bronchial tube, and then the bronchial tube and the reinforcement material can be stapled using a surgical stapler. A sealant can be introduced into the bronchial tube and can harden therein, thereby helping to seal the bronchial tube where the bronchial tube was stapled. Prior to hardening, the sealant can seep or wick in a first state into the staple line, thereby facilitating complete sealing of the bronchial tube. The reinforcement material and the sealant can cooperate to provide a better, more complete seal of the staple line than if either of the reinforcement material and the sealant were used without the other. The reinforcement material at the staple line can cause inflammation of the bronchial tube, thereby causing the bronchial tube to encapsulate the reinforcement material as an irritant. Such encapsulation can facilitate long term sealing of the bronchial tube. The reinforcement material can thus take advantage of the bronchial tube's natural inflammatory response, and natural slow healing of the bronchial tube, to help seal the stapled bronchial tube. The sealant can facilitate short term sealing of the bronchial tube during the time the bronchial tube reacts to and encapsulates the reinforcement material, e.g., for a time period of up to about two weeks. The reinforcement material that has been stapled can extend from the staple line into the bronchial tubes passageway, thereby providing the sealant with a structure within the bronchial tube to help hold the sealant in position adjacent the applied staples while the sealant hardens within the bronchial tube and to help hold the sealant in position adjacent the applied staples after the sealant has hardened. By being held adjacent to the staple line by the reinforcement material, the sealant can be more likely to harden at and completely seal the staple line. The bronchial tube can thus be more likely to remain sealed during expansion and contraction of the lung during breathing.

The sealant can be introduced into the bronchial tube before the stapling of the bronchial tube and the reinforcement material, such as by the reinforcement material being imbibed with the sealant in a first state, e.g., as a softened state such as fluid, a gel, etc., or as a dry state, e.g., as a powder, etc. The reinforcement material being coupled to the sealant before stapling can facilitate delivery of the reinforcement material and the sealant into the bronchial tube by allowing the reinforcement material and the sealant to be simultaneously delivered thereto. Alternatively or in addition, the sealant can be introduced into the bronchial tube after the stapling of the bronchial tube and the reinforcement material, such as by injection of the sealant in a first state into the bronchial tube adjacent a staple line formed by the stapling. The sealant being delivered into the bronchial tube subsequent to the stapling can help prevent the sealant from hardening within the bronchial tube before the bronchial tube is stapled. If the sealant is delivered into the bronchial tube subsequent to the stapling, the same surgical instrument that delivered the reinforcement material into the bronchial tube can deliver the sealant, thereby making the surgical procedure easier to perform since only one delivery device need be introduced into the bronchial tube.

Figure 1:
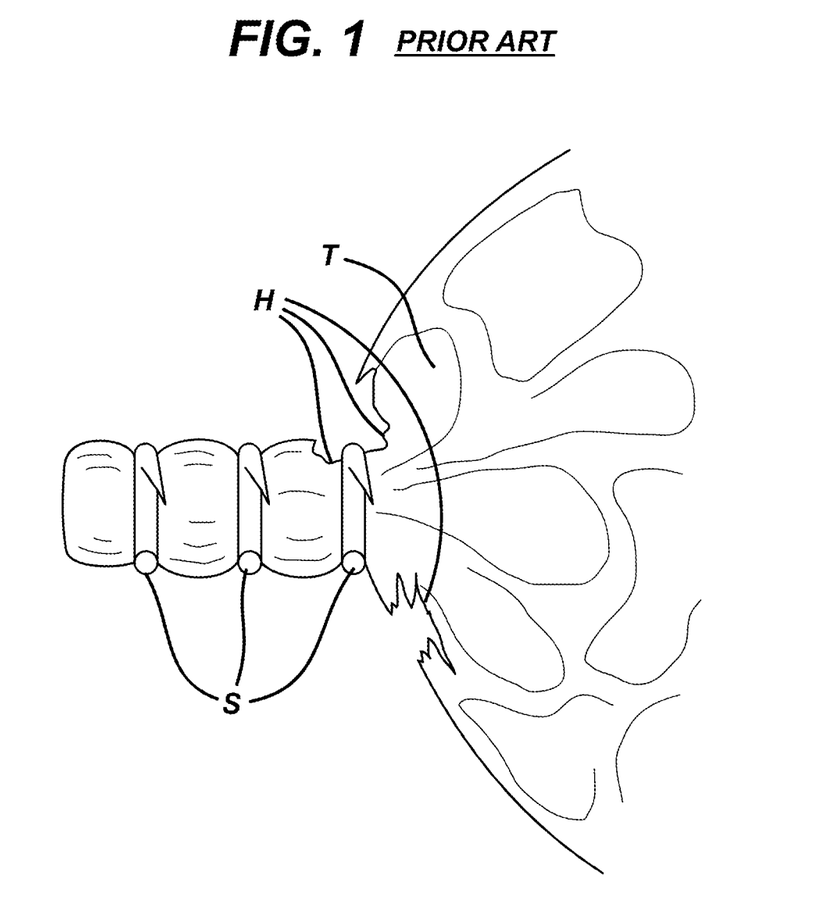
FIG. 1 is a side view of damaged stapled tissue.
Figure 2:
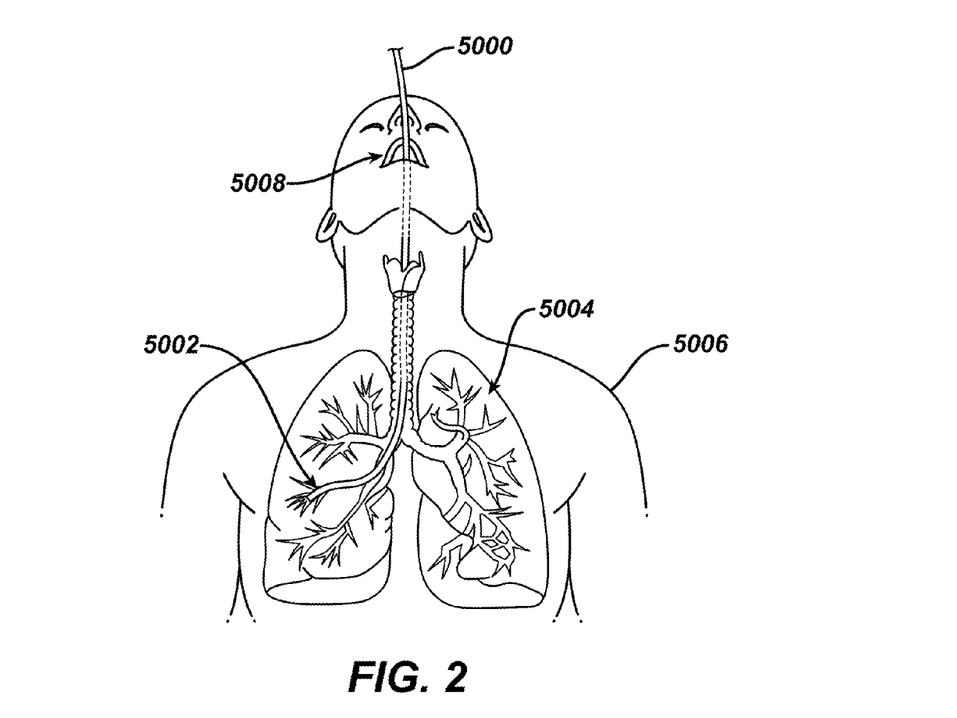
FIG. 2 is a perspective, partially transparent view of a patient with one embodiment of a surgical instrument transorally advanced into a bronchial tube of the patient.

FIG. 2 illustrates one embodiment of a surgical instrument 5000 configured to deliver a reinforcement material (not shown) and a sealant (not shown) into a bronchial tube 5002 of lungs 5004 of a patient 5006. The instrument 5000 can include a proximal handle portion (not shown) configured to be held, e.g., handheld by a medical practitioner, held by a robotic surgical arm, etc., outside the patient 5006, as will be appreciated by a person skilled in the art. The instrument 5000 can be configured to be transorally advanced into the bronchial tube 5002, as shown in FIG. 2, by being advanced into a mouth 5008 of the patient 5006. The instrument 5000 can be advanced into the patient 5006 in other ways, as will be appreciated by a person skilled in the art. For example, the instrument 500 can be configured to be advanced into a patient through an introducer device, such as a trocar, inserted into the patient through an incision formed through skin of the patient.

Figure 3:
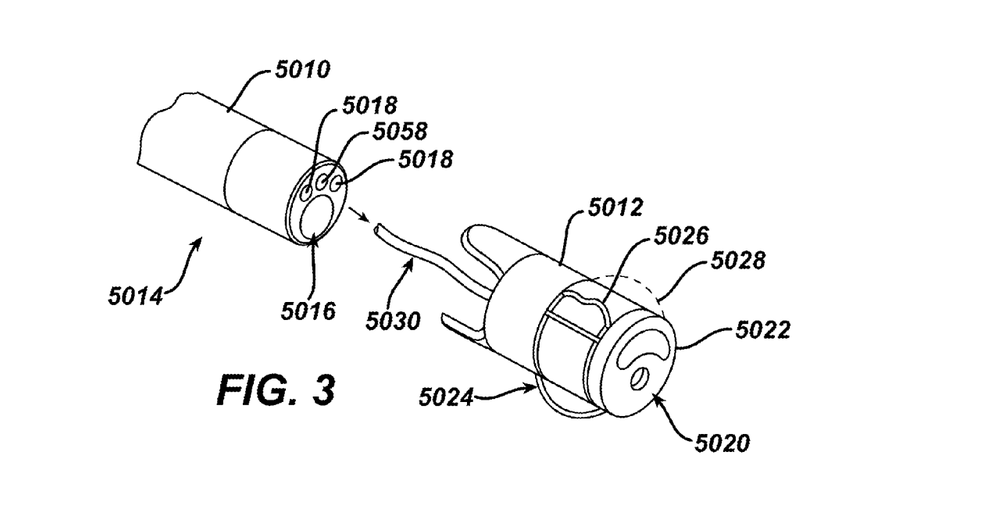
FIG. 3 is an exploded perspective view of a distal end of the surgical instrument of FIG. 2 including a scoping device and an end cap.

As shown in FIG. 3, the instrument 5000 can include a scoping device 5010, e.g., an endoscope, a laparoscope, etc., and an end cap 5012 configured to be coupled to a distal end 5014 of the scoping device 5010. The scoping device 5010 in this illustrated embodiment has one working channel 5016 extending longitudinally therethrough, includes one visualization element 5058, e.g., a lens, etc., and includes two lights 5018, e.g., light emitting diodes (LEDs), etc. The lights 5018 and the viewing element 5058 can be distal-facing, as in the illustrated embodiment, which can facilitate visualization of a target surgical site distal to the instrument 5000. In other embodiments, a scoping device can have a plurality of working channels extending longitudinally therethrough and/or can have a different number of lights.

The end cap 5012 can be configured to be selectively attachable to the scoping device's distal end 5014, such as by being snap fit thereon, by being fit thereto via interference fit (as in the illustrated embodiment), by being threaded thereto, etc. In other words, the end cap 5012 can be configured to be removably and replaceably attachable to the scoping device 5010. The end cap 5012 being configured to be selectively attachable to the scoping device 5010 can allow the end cap to be disposable, can facilitate cleaning of the scoping device 5010 and/or the end cap 5012 before reuse with another patient, and/or can help prevent the scoping device 5010 from being damaged by sealant delivered using the instrument 5000. Exemplary embodiments of attachment techniques for attaching an end cap to a scoping device are described in further detailed in U.S. Pat. No. 8,551,058 entitled "Endoscopic Translumenal Surgical Systems" filed on Jul. 10, 2007, which is hereby incorporated by reference in its entirety.

The end cap 5012 can include a working port 5020, a window 5022, and a balloon 5024 around a perimeter thereof. The working port 5020 can be configured to be aligned with the scoping device's working channel 5016 when the end cap 5012 is attached to the scoping device 5010, which can allow a surgical device (not shown) to be advanced distally through the scoping device's working channel 5016 and through the end cap's working port 5020. The window 5022 can be configured to be aligned with the scoping device's lights 5018 when the end cap 5012 is attached to the scoping device 5010, thereby allowing the lights 5018 to shine through the window 5022 so as to illuminate a target surgical site distal to the instrument 5000.

The balloon 5024 can be configured to be selectively inflatable when the end cap 5012 is attached to the scoping device 5010. The balloon 5024 can be configured to move between an uninflated configuration, shown in FIG. 3 with the balloon 5024 in solid line 5026, and an inflated configuration, shown in FIG. 3 with the balloon 5024 in broken line 5028. When the balloon 5024 is in the uninflated configuration, the end cap 5012 can have a first diameter that is less than a second diameter of the end cap 5012 when the balloon 5024 is in the inflated configuration. The balloon 5024 can be configured to be selectively inflated and deflated in a variety of ways. As in this illustrated embodiment, the end cap 5012 can include an inflation line 5030 extending distally therefrom. The balloon 5024 can be in fluid communication with the inflation line 5030. The inflation line 5030 can be configured to extend through the working channel 5016 of the scoping device 5010 and couple to an inflation source (not shown) at a proximal end of the scoping device 5010, as will be appreciated by a person skilled in the art. In some embodiments, the inflation line 5030 can extend through the working channel 5016 of the scoping device 5010 and be configured to be attached to the end cap 5012 when the end cap 5012 is attached to the distal end 5014 of the scoping device 5010.

The end cap 5012 can include a cleaning mechanism (not shown) configured to clean a distal end of the instrument 5000, e.g., a distal end of the scoping device 5010 and/or a distal end of the end cap 5012, when the end cap 5012 is attached to the scoping device's distal end. The cleaning mechanism can allow for the instrument 5000 to be cleaned within a patient's body such that the instrument 5000 need not be removed for cleaning should the viewing element 5058, the lights 5018, and/or other feature become obscured, clogged, etc. during use due to fluid and/or other matter. Exemplary embodiments of cleaning mechanisms are described in further detailed in U.S. Pat. Pub. No. 2009/0270686 entitled "Methods And Devices For Maintaining Visibility During Surgical Procedures" filed on Apr. 29, 2008, and U.S. Pat. Pub. No. 2009/0234193 entitled "Apparatus For Keeping Clean A Distal Scope End Of A Medical Viewing Scope" filed on Mar. 13, 2008, which are hereby incorporated by reference in their entireties.

FIGS. 4-7 illustrate an exemplary embodiment of a surgical procedure for stapling and sealing the bronchial tube 5002 using the instrument 5000. Although the procedure is illustrated with respect to the surgical instrument 5000 of FIGS. 2 and 3, any of the surgical instruments discussed herein can be similarly used. Similarly, although the procedure is illustrated with respect to the bronchial tube 5002 of FIG. 2, another tubular anatomical structure, e.g., a blood vessel, etc., can be similarly treated. Also, although the procedure is illustrated with respect to stapling, a bronchial tube (or other anatomical structure) can be sealed as discussed herein in conjunction with a type of fastener other than staples, e.g., clips, sutures, energy, etc.

Figure 4:
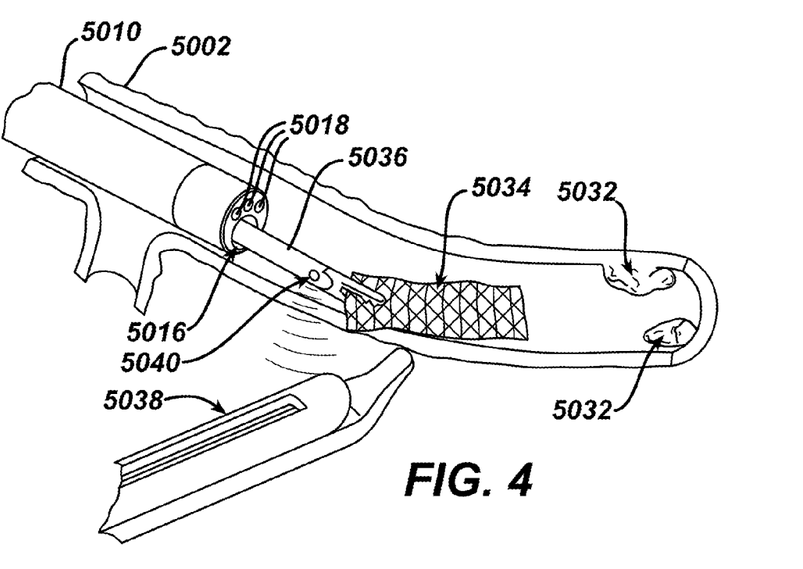
FIG. 4 is a perspective, partially cross-sectional view of the scoping device of FIG. 3 advanced into the bronchial tube of FIG. 2, one embodiment of a grasper advanced through a working channel of the scoping device and grasping one embodiment of a reinforcement material, and one embodiment of a stapler having a distal end positioned outside and adjacent to the bronchial tube.

As shown in FIG. 4, the bronchial tube 5002 can include a tumor 5032. As will be appreciated by a person skilled in the art, treatment of the tumor 5032 can include removing a portion of the bronchial tube 5002 that includes the tumor 5032 and leaving another portion of the bronchial tube 5002 within the patient 5006.

As also shown in FIG. 4, a reinforcement material 5034 can be introduced into the bronchial tube 5002. The reinforcement material 5034 can include a flexible material configured to be stapled or otherwise fastened, e.g., using clips, etc., within the bronchial tube 5002. Examples of the reinforcement material 5034 include a mesh (e.g., a knitted mesh, a non-woven mesh, or a woven mesh), a non-woven matrix, a composite matrix including a non-woven polymer (e.g., polyglactin 910) and a knitted or woven backing material (e.g., oxidized cellulose), a film, a melt-blown non-woven material, a felt material, a closed-cell foam, an open-cell foam, a sponge, a braided suture, and oxidized cellulose (e.g., oxidized regenerated cellulose (ORC)). Various embodiments of multilayered dressings that can be used as the reinforcement material 5034 are described in U.S. Pat. Pub. No. 2006/0257458 entitled "Reinforced Absorbable Multilayered Hemostatis Wound Dressing" filed on Apr. 10, 2006, which is hereby incorporated by reference in its entirety. The reinforcement material 5034 can be absorbable or non-absorbable. The reinforcement material 5034 in this illustrated embodiment includes a mesh. The mesh can be formed from any one or more materials. In general, material suitable for implantation, such as material for a surgical suture, can be suitable for the mesh. Examples of absorbable materials that can be used, alone or in any combination thereof, to form the mesh include poliglecaprone (e.g., Monocryl® available from Ethicon, Inc. of Somerville, N.J.), polyglactin (e.g., polyglactin 910, such as Vicryl® available from Ethicon, Inc. of Somerville, N.J.), polydioxanone, collagen, oxidized cellulose, glycerol, glycolide, lactide, dioxanone, trimethylene carbonate, and gut suture. Examples of non-absorbable materials that can be used, alone or in any combination thereof, to form the mesh include polypropylene, polyethylene, polybutester fiber, stainless steel, nylon, polyester, silk, and polyvinylidene difluoride (PVDF). The reinforcement material 5034 in this illustrated embodiment has a rectangular shape, but the reinforcement material 5034 can have any shape, e.g., ovular, triangular, etc.

The reinforcement material 5034 can be introduced into the bronchial tube 5002 by being advanced through the working channel 5016 of the scoping device 5010, as also shown in FIG. 4. The end cap 5012 is not attached to the scoping device 5010 in FIG. 4. A grasper 5036 grasping the reinforcement material 5034 can be advanced through the scoping device's working channel 5016 so as to hold and pass the reinforcement material 5034 through the working channel 5016 and out a distal end thereof so as to position the reinforcement material 5034 within the bronchial tube 5002, as shown in FIG. 4. The reinforcement material 5034 can be introduced into the bronchial tube 5002 in another way, as will be appreciated by a person skilled in the art, such as by being advanced through a different scoping device, advancing the reinforcement material 5034 into the bronchial tube 5002 using the grasper 5036 without a scoping device, etc.

The reinforcement material 5034 can be positioned at a target site within the bronchial tube 5002 located on one side of the tumor 5032. The target site can be an area intended to be stapled with a surgical stapler 5038. The stapler 5038 can be any surgical stapler configured to staple a bronchial tube, such as a linear stapler, as shown in the illustrated embodiment. Exemplary embodiments of staplers are described in further detail in U.S. patent application Ser. No. 14/300,954 entitled "Adjunct Materials and Methods of Using Same in Surgical Methods for Tissue Sealing" filed on Jun. 10, 2014, which is hereby incorporated by reference in its entirety.

The stapler 5038 can be located outside the bronchial tube 5002, as shown in FIG. 4. The stapler 5038 and the grasper 5036 can include a location mechanism configured to help position the stapler 5038 relative to the target site within the bronchial tube 5002 where the reinforcement material 5034 is positioned. The bronchial tube 5002 is a relatively hard member that can make it difficult, if not impossible, to locate the grasper 5036 and/or the reinforcement material 5034 therein by touch. In another, softer body lumen, such as the intestinal tract, the grasper 5036 and/or the reinforcement material 5034 could be located by external touch of the lumen, e.g., by touching the lumen with a finger, by gently pressing the stapler 5038 against the lumen, etc.

The location mechanism can have a variety of configurations. Exemplary embodiments of location mechanisms that can be used to facilitate positioning of a stapler are described in U.S. Pat. Pub. No. 2012/0024934 entitled "Transwall Visualization Arrangements And Methods For Surgical Circular Staplers" filed on Jul. 30, 2010, which is hereby incorporated by reference in its entirety.

For example, the location mechanism can include a light illuminated within the bronchial tube 5002 that can be detectable from outside the bronchial tube 5002. For example, the lights 5018 of the scoping device 5010 can be configured to be bright enough to be visually detectable from outside the bronchial tube 5002. For another example, the location mechanism can include a light (not shown) illuminated from outside the bronchial tube 5002 that can allow location of the grasper 5036 and/or the reinforcement material 5034 within the bronchial tube 5002 to be visually identified, such as by the stapler 5038 including a light (not shown) and/or a second scoping device (not shown) located outside the bronchial tube 5002 including one or more lights similar to the lights 5018 of the scoping device 5010. For yet another example, the location mechanism can include one or more magnets, such as rare earth magnets, located within the bronchial tube 5002, e.g., by being attached to the grasper 5036, by being attached to detection members (e.g., lights, extendable bumpers, etc.) coupled to the scoping device 5010, etc. A probe (e.g., a Hall effect sensor, etc.) positioned near the tumor 5032 side of the bronchial tube 5002 can be configured to measure a distance between the magnet(s) and the tumor 5032, thereby indicating a location for stapling of the bronchial tube 5002. The probe can be attached to the stapler, e.g., to a distal tip of an anvil of the stapler. The magnet(s) can be configured to alternate in polarity and/or vary in intensity, which can facilitate the probe's measurement of the distance by allowing the probe to detect distance and orientation.

In this illustrated embodiment, the location mechanism includes a magnet 5040 coupled to the grasper 5036 and a sensor (not shown), e.g., a proximity sensor, a Hall effect sensor, etc., coupled to the stapler 5038 and configured to sense the magnet 5040 coupled to the grasper 5036 when the sensor is within a certain predetermined distance of the magnet 5040. In this way, the sensor being positioned near the magnet 5040 disposed within the bronchial tube 5002, so as to sense the magnet 5040, can indicate that the stapler 5038 is adjacent the reinforcement material 5034 within the bronchial tube 5002. In other words, the detection of the magnet 5040 by the sensor can indicate that the stapler 5038 is at a position relative to the bronchial tube 5002 at which the stapler 5038 can staple the bronchial tube 5002. The sensor sensing the magnet 5040 can be configured to trigger a notification at a proximal end (not shown) of the stapler 5038 when the stapler's magnet is magnetically attracted to the magnet 5040, which can help indicate to a user of the stapler 5038 that the stapler 5038 is positioned adjacent the target site. The notification can include, e.g., a light, a sound, a vibration, etc. The grasper 5036 includes one magnet 5040 in this illustrated embodiment, but the grasper 5036 can each include any number of magnets. Although the grasper 5036 includes the magnet 5040 in this illustrated embodiment, another element, such as the scoping device 5010 (e.g., the distal end 5014 thereof), the reinforcement material 5034, etc., can include the magnet 5040 and/or can include one or more additional magnets. In an exemplary embodiment, the magnet 5040 can be coupled to an element that is not implanted within the bronchial tube 5002, e.g., on a surgical device used to deliver the reinforcement material 5034 and/or a sealant to the bronchial tube 5002, which can help prevent the location mechanism from interfering with any subsequent surgical procedures.

Figure 5:
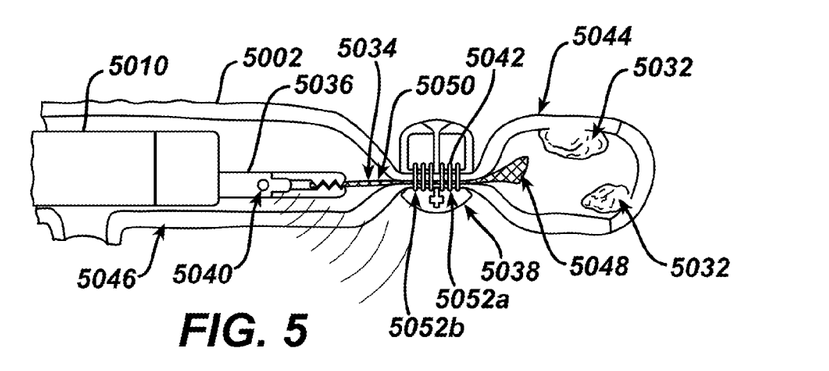
FIG. 5 is a perspective, partially cross-sectional view of the stapler of FIG. 4 stapling the bronchial tube and the reinforcement material.
Figure 6:
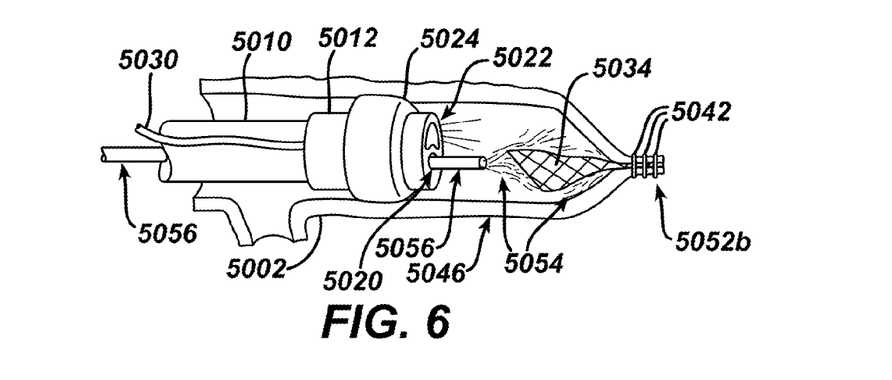
FIG. 6 is a perspective, partially cross-sectional view of the scoping device of FIG. 3, with the end cap of FIG. 3 attached thereto, within a portion of the bronchial tube of FIG. 5 stapled and cut by the stapler, and one embodiment of an applicator advanced through the working channel of the scoping device and a working port of the end cap, the applicator applying one embodiment of a sealant, the sealant being in a first state.

When the stapler 5038 is positioned at a desired location relative to the bronchial tube 5002, e.g., adjacent the target site where the reinforcement material 5034 is within the bronchial tube 5002, the stapler 5038 can staple the bronchial tube 5002 and the reinforcement material 5034 by ejecting one or more staples 5042 therefrom, as shown in FIG. 5. The stapler 5038 in this illustrated embodiment ejects six staples 5042, but the stapler 5038 can eject any number of staples, simultaneously or sequentially. The stapler 5038 can also, as will be appreciated by a person skilled in the art, cut the stapled bronchial tube 5002 using a knife or other cutting element. The cutting of the bronchial tube 5002 can result in a specimen portion 5044 of the bronchial tube 5002, which includes the tumor 5032 and which can be removed from the patient 5006, and a remainder portion 5046 of the bronchial tube 5002, which can remain within the patient 5006. As shown in FIG. 6, the stapling and cutting can form first and second staple lines 5052a, 5052b in the bronchial tube, with the first staple line 5052a being formed in the specimen portion 5044 and the second staple line 5052b being formed in the remainder portion 5046.

As mentioned above, the stapler 5038 can staple the reinforcement material 5034 when the stapler 5038 staples the bronchial tube 5002. The stapler 5038 can thus cut the reinforcement material 5034 when the stapler 5038 cuts the bronchial tube 5002. A first portion 5048 of the reinforcement material 5034 can be in the specimen portion 5044 after being stapled and cut and can be removed from the patient 5006 with the specimen portion 5044. A second portion 5050 of the reinforcement material 5034 can be in the remainder portion 5046 and can remain in the bronchial tube 5002 after being stapled and cut, as shown in FIG. 6. The second portion 5050 of the reinforcement material 5034 within the bronchial tube 5002 can extend from the staple line 5052b into the bronchial tube 5002.

As shown in FIG. 6, a sealant 5054 can be introduced into the bronchial tube 5002. The sealant 5054 can include a material configured to transition from a first state to a second state in which the material is harder than in the first state. The first state can thus be a softened state or a dry state, and the second state can be a second, harder state, e.g., hardened as a solid, a rigid member. The sealant 5054 can be configured to transition from the first state to the second, harder state in a predetermined amount of time. As will be appreciated by a person skilled in the art, the predetermined amount of time can vary based on the substance(s) forming the sealant 5054. Examples of the sealant 5054 include one or a combination of one or more of an adhesive, fibrin thrombin, a hydrogel, fibronectin, gelatin, collagen, Factor XIII, transglutaminase, polyethylene glycol (e.g., Progel® Pleural Air Leak Sealant available from Davol Inc. of Providence, R.I.), alginate, carboxymethylcellulose, methylcellulose, hydroxypropylmethyl cellulose, pectin, polyvinyl alcohol, polyvinylpyrrolidone, benzocaine (e.g., Projel-20™ available from Septodont of Lancaster, Pa.), cyanoacrylate, polyglycolic acid, hyaluronic acid, magnesium peroxide, 2 octyl cyanoacrylate (e.g., Dermabond® available from Ethicon, Inc. of Somerville, N.J.), and hydrogen peroxide. In another embodiment, the sealant can be blood, such as autologous blood. Exemplary embodiments of sealants are described in further detail in U.S. patent application Ser. No. 14/300,820 entitled "Methods And Devices For Sealing A Body Lumen" filed on Jun. 10, 2014, which is hereby incorporated by reference in its entirety.

The sealant 5054 can be introduced into the bronchial tube 5002 by being advanced through the working channel 5016 of the scoping device 5010, as also shown in FIG. 6. The sealant 5054 can be advanced into the bronchial tube 5002 in the first state, as also shown in FIG. 6.

The end cap 5012 can be attached to the scoping device 5010 when the sealant 5054 is delivered into the bronchial tube 5002, as also shown in FIG. 6. If the end cap 5012 is not already attached to the scoping device 5010, e.g., when the reinforcement material 5034 is introduced into the bronchial tube 5002, the scoping device 5010 can be removed from the bronchial tube 5002 after delivering the reinforcement material 5034, and the end cap 5012 can be attached to the distal end 5014 of the scoping device 5010. The end cap 5012 being attached to the scoping device 5010 when the sealant 5054 is delivered into the bronchial tube 5002 can help protect the scoping device 5010 from damage by helping to keep the sealant 5054 from contacting the scoping device 5010 and hardening thereon. Hardened sealant 5054 on the scoping device 5010 can cause damage to the scoping device 5010 by, e.g., clogging the working channel 5016 and/or obscuring the lights 5018. If the sealant 5054 contacts the end cap 5012 and hardens thereon, the end cap 5012 can be disposed of at typically much lower monetary cost than disposing the scoping device 5010 and/or the end cap 5012 can be more easily cleaned than the scoping device 5010 since, e.g., the end cap 5012 is smaller than the endoscope 5010.

An applicator 5056 can be slidably advanced through the scoping device's working channel 5016 and deliver the sealant 5054 therethrough. The applicator 5056 can have a variety of configurations. In this illustrated embodiment, the applicator 5056 includes an elongate tube through which the sealant 5054 can pass.

The sealant 5054 can be directed toward the staple line 5052b. The sealant 5054 can thus be directed toward the second portion 5050 of the reinforcement material 5034 extending from the staple line 5052b. The applicator 5056 can be advanced through the scoping device's working channel 5016 and out the end cap's working port 5020, as shown in FIG. 6, to facilitate directing the sealant 5054 toward the reinforcement material 5034. The lights 5018 of the scoping device 5010 can be on and can shine through the end cap's window 5022, as shown in FIG. 6, which can facilitate visualization of the applicator 5056, the reinforcement material 5034, and/or the sealant 5054 using the viewing element 5058, which can help the sealant 5054 be directed toward the staple line 5052b.

The sealant 5054 can be introduced into the bronchial tube 5002 so as to be applied to the reinforcement material 5034 and/or an interior tissue surface of the bronchial tube 5002. The reinforcement material 5034 can provide an object within the bronchial tube 5002 for the sealant 5054 to attach to, thereby helping to ensure that the sealant 5054 hardens adjacent the staple line 5052b, thereby helping to seal the staple line 5052b. In an exemplary embodiment, the sealant 5054 is applied to both the reinforcement material 5034 and the interior tissue surface of the bronchial tube 5002, as shown in FIGS. 6 and 7.

Figure 7:
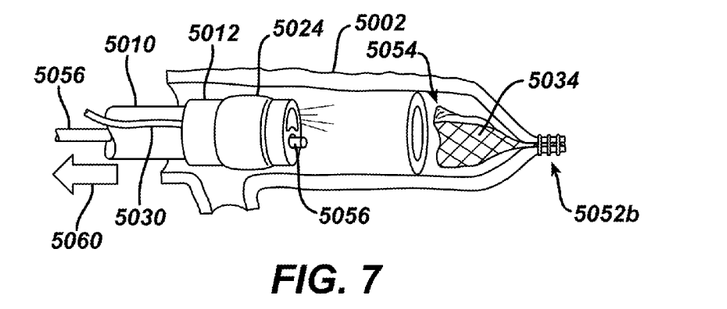
FIG. 7 is a perspective, partially cross-sectional view of the scoping device and the end cap of FIG. 6 being removed from the bronchial tube with the applied sealant being in a hardened state.

The sealant 5054 can be configured to transition from the first state in which it is delivered into the bronchial tube 5002, as shown in FIG. 6, to the second, harder state, as shown in FIG. 7. The sealant 5054 being introduced into the bronchial tube 5002 in the first state can allow the sealant 5054 to seep or wick into the staple line 5052b and into the reinforcement material 5034, which can facilitate sealing of the staple line 5052b so as to help prevent a leak. The sealant 5054 in the hardened state being coupled to the reinforcement material 5034, as shown in FIG. 7, can help keep the sealant 5054 in position within the bronchial tube 5002 where the sealant 5054 is helping to seal the staple line 5052b.

The balloon 5024 can be in the inflated within the bronchial tube 5002 when the sealant 5054 is being advanced out of the applicator 5056, as shown in FIG. 6. In other words, the balloon 5024 can be in the inflated configuration during delivery of the sealant 5054 into the bronchial tube 5002. The balloon 5024 being inflated during delivery of the sealant 5054 can help prevent the sealant 5054 from blowing back proximally after being advanced distally from the applicator 5056 by filling any excess space between the end cap 5012 and the interior surface of the bronchial tube 5002, can help prevent the sealant 5054 from hardening within the bronchial tube 5002 at a location that could potentially interfere with the bronchial tube's ordinary function during breathing, can help hold the end cap 5012 in a fixed position relative to the bronchial tube 5002 during delivery of the sealant 5054 so as to facilitate introduction of the sealant 5054 into the bronchial tube 5002 at a desired location, and/or can help direct all of the sealant 5054 toward the staple line 5052b.

The balloon 5024 can be in the uninflated configuration when the end cap 5012 is advanced into bronchial tube 5002 and can be moved from the uninflated configuration to the inflated configuration after the end cap 5012 has been positioned within the bronchial tube 5002 adjacent the staple line 5052b. The balloon 5024 can be expanded within the bronchial tube 5002 using the inflation line 5030, e.g., by passing a fluid (e.g., air, water, etc.) through the inflation line 5030 and into the balloon 5024. The balloon 5024 being in the uninflated configuration during advancement of the end cap 5012 through the patient's mouth 5008 and through advancement of the end cap 5012 to the target site within the bronchial tube 5002 can allow the end cap 5012 to have a smaller outer diameter, which can facilitate passage of the end cap 5012 through the patient's body.

If the end cap 5012 is attached to the scoping device 5010 when the reinforcement material 5034 is advanced into the bronchial tube 5002, the balloon 5024 can be in the inflated configuration when the reinforcement material 5034 is being advanced into the bronchial tube 5002. The balloon 5024 being inflated during delivery of the reinforcement material 5034 can help prevent the reinforcement material 5034 from blowing back proximally after being advanced distally from the scoping device 5010 by filling any excess space between the end cap 5012 and the interior surface of the bronchial tube 5002 and/or can help hold the end cap 5012 in a fixed position relative to the bronchial tube 5002 during delivery of the reinforcement material 5034 so as to facilitate positioning the reinforcement material 5034 at a desired location.

After the sealant 5054 has been delivered into the bronchial tube 5002, the scoping device 5010, the end cap 5012 (if attached to the scoping device 5010 during sealant 5054 delivery), and any devices within the scoping device's working channel 5016, e.g., the applicator 5056, can be removed from the bronchial tube 5002. FIG. 7 shows the removal of the scoping device 5010, the end cap 5012, and the applicator 5056 from the bronchial tube 5002 in a direction shown by a retraction arrow 5060. The applicator 5056 is removed from the bronchial tube 5002 simultaneously with the scoping device 5010 and the end cap 5012 in this illustrated embodiment, but the applicator 5056 can be removed from the bronchial tube 5002 before the scoping device 5010 and the end cap 5012, e.g., by being withdrawn from the working channel 5016. Although FIG. 7 shows the scoping device 5010, the end cap 5012, and the applicator 5056 being removed from the bronchial tube 5002 after the sealant 5054 has transitioned from the first state to the second, harder state, any of the scoping device 5010, the end cap 5012, and the applicator 5056 can be removed prior to the sealant 5054 completing the transition to the hardened state. Keeping at least the scoping device 5010 within the bronchial tube 5002 until the sealant 5054 has transitioned to the hardened state can help ensure that the sealant 5054 hardens in the proper location adjacent the staple line 5052b, e.g., by allowing visualization of the sealant 5054 within the bronchial tube 5002 using the viewing element 5058.

In some embodiments, the reinforcement material 5034 can include sealant coupled thereto prior to the reinforcement material 5034 being stapled. For example, the reinforcement material 5034 can have a sealant coupled thereto, e.g., imbibed therein, soaked therein, coated thereon, etc., when the reinforcement material 5034 is advanced into the bronchial tube 5002. For another example, the reinforcement material 5034 can include a composite matrix (e.g., the composite matrix mentioned above including a non-woven polymer and a knitted or woven backing material) coated or impregnated with a sealant such as lyophilized fibrinogen and thrombin, a non-woven support. By the reinforcement material 5034 including sealant prior to the stapling thereof, the surgical procedure can include fewer steps since sealant need not be separately delivered after the stapling. However, even if the reinforcement material 5034 includes sealant prior to the stapling thereof, sealant can be delivered after the stapling, which can help ensure complete sealing of the staple line 5052b. For example, sealant coupled to the reinforcement material 5034 can include a first component, and sealant delivered subsequent to delivery of the reinforcement material 5034 can include a second component configured to activate the first component when in contact therewith. The second component activating the first component can trigger the transitioning from the first state to the hardened state so as to create a third material that acts as the sealant. In this way, timing of hardening of the sealant can be user-controlled by preventing hardening of the sealant until the second component is introduced to the first component, which can help prevent premature hardening of the sealant before the reinforcement material 5034 is desirably positioned and/or before stapling occurs. Delivering the sealant as multiple components can ease delivery of the sealant through the relatively small diameter bronchial tube 5002 by allowing the sealant to be introduced therein in multiple parts. In other words, less sealant material can be passed through the tube 5002 at any given time. Delivering the sealant as multiple components can be less expensive monetarily than introducing a singular sealant material into the bronchial tube 5002 since amounts of the sealant introduced can be better controlled and/or less of a more expensive component can be introduced than a less expensive component. Exemplary embodiments of multi-component sealants configured to be activated are described in further detail in previously mentioned U.S. patent application Ser. No. 14/300,820 entitled "Methods And Devices For Sealing A Body Lumen" filed on Jun. 10, 2014, which is hereby incorporated by reference in its entirety.

Figure 8:
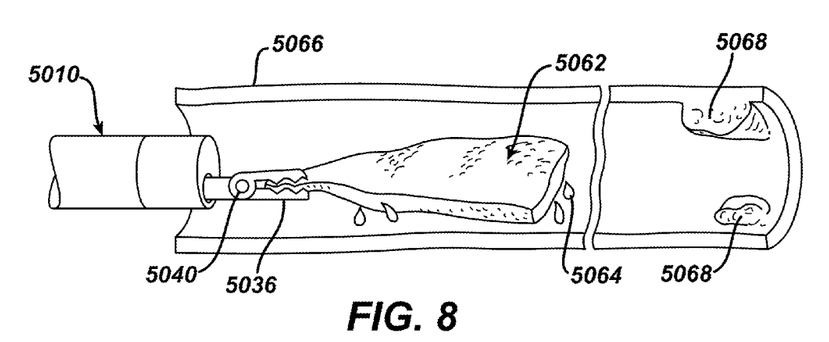
FIG. 8 is a perspective, partially cross-sectional view of the scoping device of FIG. 3 disposed within a bronchial tube and the grasper of FIG. 4 advanced through the working channel of the scoping device and grasping another embodiment of a reinforcement material coupled to another embodiment of a sealant.
Figure 9:
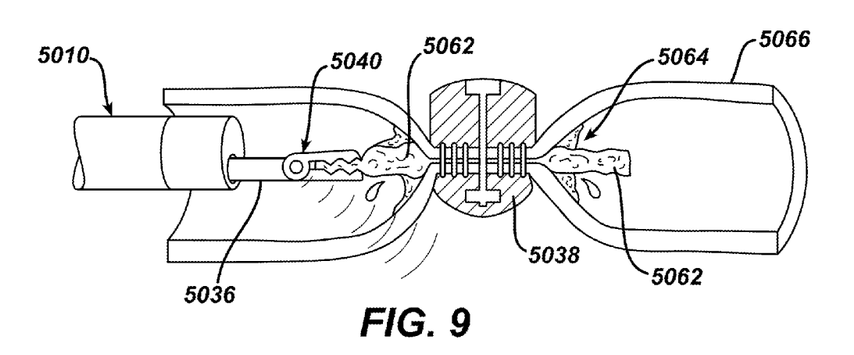
FIG. 9 is a perspective, partially cross-sectional view of the stapler of FIG. 4 stapling the bronchial tube, the reinforcement material, and the sealant of FIG. 8.

FIGS. 8 and 9 illustrate another embodiment of a reinforcement material 5062 and a sealant 5064. In this illustrated embodiment, as shown in FIG. 8, the reinforcement material 5062 is coupled to the sealant 5064 prior to stapling of the reinforcement material 5062 and a bronchial tube 5066 within which the reinforcement material 5062 can be positioned. The reinforcement material 5062 in this illustrated embodiment includes a sponge. The sealant in 5064 in this illustrated embodiment includes a therapeutic agent, e.g., a biologic, soaked into the sponge. The sealant 5064 being coupled to the reinforcement material 5062 prior to stapling thereof can help the sealant 5064 seal a staple line in the bronchial tube 5066 since the sealant 5064 can be positioned within the bronchial tube 5066 at a location of the staple line prior to formation of the staple line. The sealant 5064 including a therapeutic agent can help facilitate healing, as will be appreciated by a person skilled in the art.

The reinforcement material 5062 can be advanced into the bronchial tube 5066 similar to that discussed above regarding the reinforcement material 5034 of FIGS. 4-7. The scoping device 5010 of FIGS. 3-7 and the grasper 5036 of FIGS. 4 and 5 are shown advancing the reinforcement material 5062 into the bronchial tube 6066, but these and/or other devices can be used to introduce the reinforcement material 5062 into the bronchial tube 5066, as discussed above. Similarly, the stapler 5038 of FIGS. 4 and 5 is shown stapling the bronchial tube 5066, the reinforcement material 5062, and the sealant 5064 in FIG. 9, but a different stapler or a device applying a different type of fastener can be used to cut and secure a portion of the bronchial tube 5066. The bronchial tube 5066 in this illustrated embodiment has a tumor 5068 therein that is being excised, thereby prompting introduction of the reinforcement material 5062 and the sealant 5064 therein, but a bronchial tube can be treated for this and/or another reason using any reinforcement material and any sealant described herein.

The sealant 5064 can be sufficient sealant to seal the staple line formed by the stapler 5038. However, as mentioned above, additional sealant (not shown), such as an activator of the sealant 5064 previously delivered, can be introduced into the bronchial tube 5066 and delivered adjacent to the staple line so as to facilitate sealing thereof. The additional sealant can be advanced into the bronchial tube 5066 in a variety of ways, such as by the using the applicator 5056 of FIGS. 6 and 7 discussed above.

In some embodiments, a bronchial tube can be stapled, or otherwise cut and fastened, before a reinforcement material or a sealant are introduced into the bronchial tube. Stapling or otherwise fastening the bronchial tube before introducing the reinforcement material or the sealant are introduced therein can allow the bronchial tube to be stapled without a chance of the bronchial tube being stapled at a location where the reinforcement material is not positioned.

Figure 10:
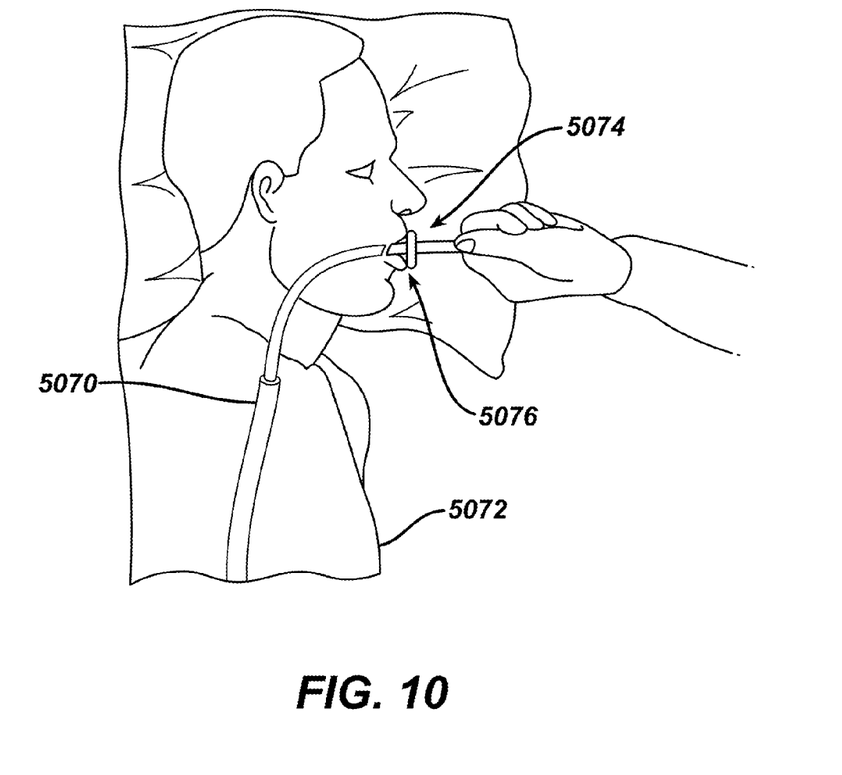
FIG. 10 is a perspective, partially transparent view of another patient with another embodiment of a surgical instrument transorally advanced into a bronchial tube of the patient.

FIG. 10 illustrates another embodiment of a surgical instrument 5070 configured to deliver a reinforcement material (not shown) and a sealant (not shown). The instrument 5070 can include a proximal handle portion 5074 configured to be held outside the patient 5072. The instrument 5070 can be configured to be transorally advanced into the patient 5072, as shown in FIG. 10, by being advanced into a mouth 5076 of the patient 5072, although the instrument 5070 can be advanced into the patient 5072 in other ways that will be appreciated by a person skilled in the art.

Figure 11:
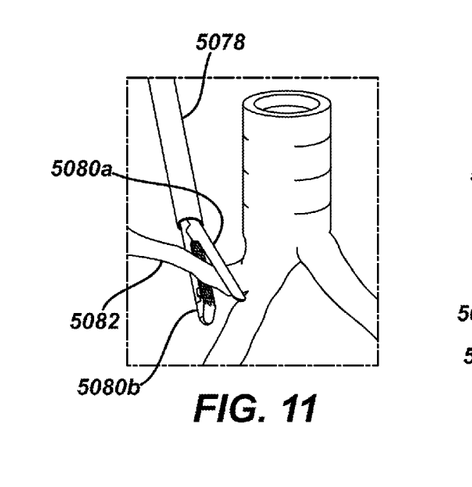
FIG. 11 is a perspective view of another embodiment of a stapler with jaws thereof positioned on either side of the bronchial tube of FIG. 10.
Figure 12:
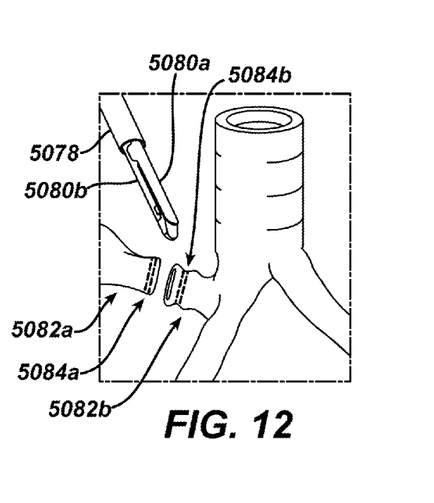
FIG. 12 is a perspective view of the bronchial tube of FIG. 11 after being stapled and cut by the stapler.

The instrument 5070 can be configured to deliver the reinforcement material and the sealant into a bronchial tube after the bronchial tube has been stapled or otherwise cut and fastened. FIG. 11 shows an embodiment of a stapler 5078 including a pair of jaws 5080*a*, 5080*b* positioned on opposite sides of a bronchial tube 5082 of the patient 5072. As mentioned above, the stapler 5078 can have a variety of configurations. FIG. 12 shows the bronchial tube 5082 after being stapled by the stapler 5078. The stapler 5078 can cut the bronchial tube 5082 when stapling and accordingly create first and second staples lines 5084*a*, 5084*b* at facing ends of the cut bronchial tube 5082. The cutting of the bronchial tube 5082 by the stapler 5078 can result in a specimen portion 5082*a* of the bronchial tube 5082, which includes the first staple line 5084*a* and can be removed from the patient 5072, and a remainder portion 5082*b* of the bronchial tube 5082, which can include the second staple line 5084*b* and can remain within the patient 5072.

Figure 13:
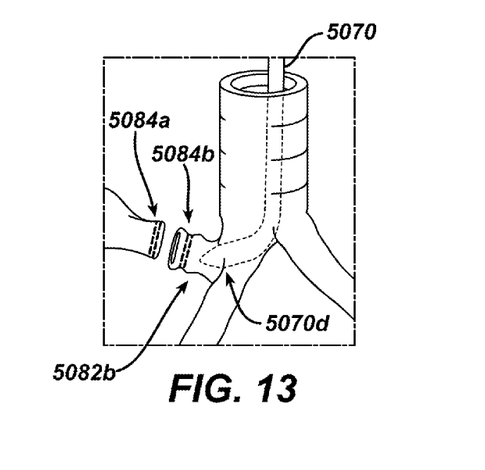
FIG. 13 is a perspective, partially transparent view of the instrument of FIG. 10 advanced into the stapled and cut bronchial tube of FIG. 12 with a distal end of the instrument positioned adjacent a stapled and cut end of the bronchial tube.
Figure 14:
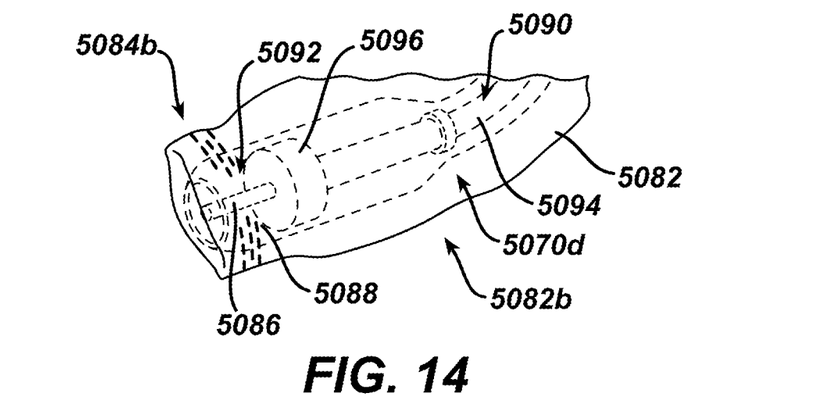
FIG. 14 is another perspective view of the distal end of the instrument of FIG. 13 positioned adjacent the stapled and cut end of the bronchial tube.

As shown in FIG. 13, the instrument 5070 can be configured to be advanced into the remainder portion 5082*b* of the bronchial tube 5082. A distal end 5070*d* of the instrument 5070, also shown in FIG. 14, can be positioned adjacent the second staple line 5084*b*. The instrument 5070 can include a first chamber 5090 configured to have a sealant 5086 disposed therein when the distal end 5070*d* is advanced into the bronchial tube 5082, and can include a second chamber 5092 configured have a reinforcement material 5088 disposed therein when the distal end 5070*d* is advanced into the bronchial tube 5082. In this illustrated embodiment, the sealant 5086 includes a fibrin and the reinforcement material 5088 includes ORC, but as mentioned above, the sealant 5086 and the reinforcement material 5088 can have other configurations. When the reinforcement material 5088 is acidic, such as when it includes ORC, the reinforcement material 5088 can provide an anti-microbial benefit during healing of the bronchial tube 5082, which can help reduce infection and/or other complications from the stapling. The first chamber 5090 in this illustrated embodiment includes a passageway of a tubular shaft 5094 extending longitudinally through the instrument 5070. The second chamber 5092 in this illustrated embodiment includes a cavity formed in a distal-most portion of the instrument 5070. The instrument 5070 can also include a piston 5096 configured to release the reinforcement material 5088 from the second chamber 5092, as discussed further below. In general, the piston 5096 can be slidably movable relative to the tubular shaft 5094 so as to move the reinforcement material 5088 out of the second chamber 5092 and out of the instrument 5070.

Figure 15:
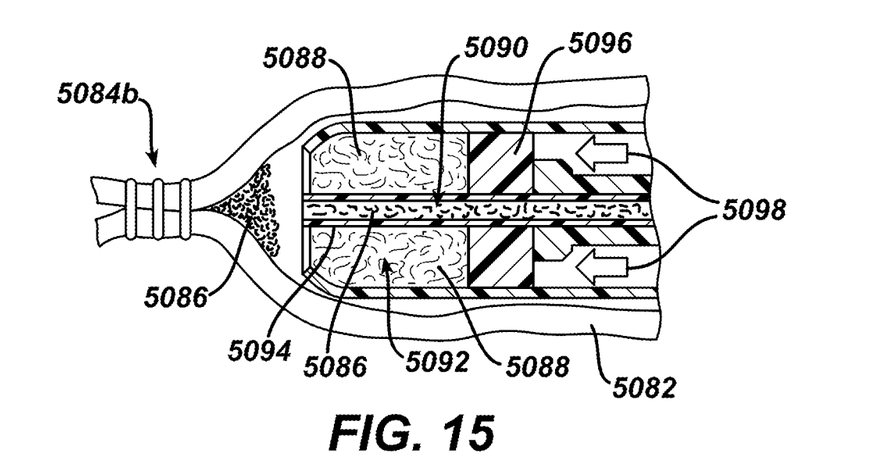
FIG. 15 is a side, cross-sectional view of the stapled and cut end of the bronchial tube of FIG. 14 having another embodiment of a sealant disposed therein, the sealant having been advanced into the bronchial tube from the instrument.

The instrument 5070 can be configured to advance the sealant 5086 and the reinforcement material 5088 into the bronchial tube 5082 adjacent the staple line 5082*b*. As shown in FIG. 15, when the instrument's distal end 5070*d* is positioned adjacent the staple line 5084*b*, the sealant 5086 can be released from the first chamber 5090 so as to be delivered into the bronchial tube 5082 at the staple line 5086. The sealant 5086 can seep or wick into the staple line 5082*b*, as discussed above. The sealant 5086 can be released from the first chamber 5090 in a variety of ways, as will be appreciated by a person skilled in the art. For example, a force can be applied to the first chamber 5090 in a distal direction, e.g., air pushed into the first chamber 5090 through an open proximal end (not shown) of the tubular shaft 5094 so as to push the sealant 5086 out a distal end of the tubular shaft 5094. All of the sealant 5086 can be released from the first chamber 5090 or, as shown in FIG. 15, only a portion of the sealant 5086 can be released from the first chamber 5090 so as to be disposed within the bronchial tube 5082.

Figure 16:
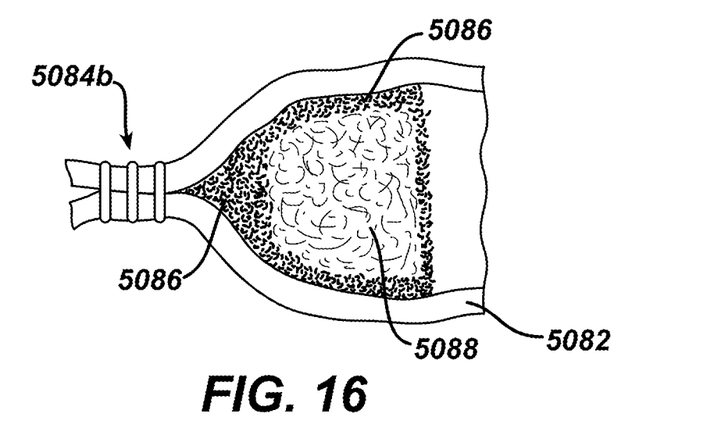
FIG. 16 is a side, cross-sectional view of the and cut end of the bronchial tube of FIG. 15 having another embodiment of a reinforcement material and additional sealant disposed therein, the reinforcement material and the additional sealant having been advanced into the bronchial tube from the instrument.

As shown in FIGS. 15 and 16, when the instrument's distal end 5070*d* is positioned adjacent the staple line 5084*b*, the reinforcement material 5088 can be released from the second chamber 5092 so as to be delivered into the bronchial tube 5082 at the staple line 5086. The reinforcement material 5088 can be released from the second chamber 5092 in a variety of ways, as will be appreciated by a person skilled in the art. For example, the piston 5096 can be advanced distally, as shown by directional arrows 5098 in FIG. 15, so as to push the reinforcement material 5088 out an open distal end of the instrument 5070. The piston 5096 can be slidably disposed around the tubular shaft 5094, as mentioned above, and slid relative thereto to release the reinforcement material 5088 without also causing release of the sealant 5086. All of the reinforcement material 5088 can be released from the second chamber 5092, as in this illustrated embodiment, or only a portion of the reinforcement material 5088 can be released from the second chamber 5092 so as to be disposed within the bronchial tube 5082.

The sealant 5086 can be applied only before the reinforcement material 5088, the sealant 5086 can be applied only after the reinforcement material 5088, or the sealant 5086 can be applied both before and after the reinforcement material 5088. Application of the sealant 5086 after the application of the reinforcement material 5088 can allow the sealant 5086 to seep or wick into any space between the reinforcement material 5088 and an internal surface of the bronchial tube 5082, thereby further facilitating sealing. In this illustrated embodiment, the sealant 5086 is applied both before and after the reinforcement material 5088. FIG. 15 shows a first application of the sealant 5086 before application of the reinforcement material 5088, and FIG. 16 shows a second application of the sealant 5086 after the application of the reinforcement material 5088.

In an embodiment in which the sealant is blood, such as autologous blood, the blood can be harvested from the patient and applied to the adjunct material. By way of non-limiting example, the adjunct material can be ORC, a known hemostatic agent, and the application of the blood to the ORC adjunct will cause the formation of a clot, resulting in an effective sealing structure. A person skilled in the art will appreciate that blood, such as autologous blood can be applied to a variety of adjunct materials to provide an enhanced sealing structure. Further, a person skilled in the art will appreciate that the volume of blood applied to the adjunct will vary depending upon a number of factors, including the type and location of tissue as well, the age and condition of the patient, and the identity of the adjunct. Generally, however, when the adjunct is an ORC material, the blood can be applied in an amount in the range of about 5-10 cc per line of staple used to affix the adjunct to the tissue.

A person skilled in the art will appreciate that the methods, devices, systems, and apparatus described herein application in conventional minimally-invasive and open surgical instrumentation as well application in robotic-assisted surgery.

Reprocessing

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

In some embodiments, devices described herein can be processed before surgery. First, a new or used instrument, which can include an adjunct material, is obtained and if necessary cleaned. The instrument can then be sterilized. In some embodiments, the instrument can be dried, e.g., in an oven, together with a desiccant item, which can have a greater affinity for moisture than the adjunct material. In one sterilization technique, the instrument is placed in a closed and sealed container, such as a plastic or TYVEK bag or a foil bag. The container and instrument are then placed in a field of radiation that can penetrate the container, such as gamma radiation, x-rays, or high-energy electrons. The radiation kills bacteria on the instrument and in the container. In another sterilization technique, the instrument is placed in a first container, such as a plastic or TYVEK bag, having a vapor permeable backing. The first container can then be packaged in a second container, e.g., a foil bag, which can be left open. The first and second containers, together with the instrument, can undergo ethylene oxide sterilization. The second container can then be sealed to prevent moisture exposure. Prior to sealing, a desiccant item may be included in at least one of the first and second containers to further prevent changes to one or more device components. In both techniques, the sterilized materials can then be stored in the sterile container(s) to keep the materials sterile until the container(s) is/are opened in the medical facility.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical method, comprising:
   transorally advancing a reinforcement material into a bronchial tube of a patient;
   introducing a sealant into the bronchial tube and applying the sealant to the reinforcement material within the bronchial tube prior to the reinforcement material being fastened to the bronchial tube, the sealant transitioning from a first state to a second, harder state within the bronchial tube so as to secure the reinforcement material in a fixed position relative to the bronchial tube; and
   after the sealant is applied to the reinforcement material, fastening the reinforcement material to the bronchial tube with a fastener;
   wherein advancing the reinforcement material includes advancing a distal end of a scoping device into the bronchial tube and introducing the reinforcement material into the bronchial tube through the scoping device;
   wherein introducing the sealant includes introducing the sealant into the bronchial tube through the scoping device with the sealant in the first state; and
   wherein the scoping device has an end cap on the distal end thereof during the introduction of the sealant into the bronchial tube through the scoping device, and the scoping device does not have the end cap on the distal end thereof during the introduction of the reinforcement material into the bronchial tube through the scoping device.

2. The method of claim 1, wherein fastening the reinforcement material includes stapling the bronchial tube and the reinforcement material that has been introduced into the bronchial tube.

3. The method of claim 2, wherein a first component of the sealant is introduced and applied before the stapling of the bronchial tube and the reinforcement material, and a second component of the sealant is introduced and applied after the stapling of the bronchial tube and the reinforcement material.

4. The method of claim 1, wherein the fastener is selected from the group consisting of staples, clips, sutures, and energy.

5. The method of claim 1, wherein the fastener includes a staple, and fastening the reinforcement material includes stapling the bronchial tube and reinforcement material using a stapler located outside of the bronchial tube.

6. The method of claim 5, wherein the stapler cuts the bronchial tube and the reinforcement material, and the method further comprises removing a cut portion of the bronchial tube and a cut portion of the reinforcement material from the patient's body.

7. A surgical method, comprising:
   positioning a reinforcement material within a bronchial tube;

positioning a stapler outside the bronchial tube and using a location mechanism coupled to the stapler to identify a location of the reinforcement material within the bronchial tube; and after identifying the location of the reinforcement material, stapling the bronchial tube and the reinforcement material with the stapler so as to form a staple line extending across the bronchial tube with the reinforcement material engaged within the staple line;

wherein an actuator coupled to the reinforcement material moves from a first state to a second, harder state after the stapling so as to facilitate sealing of the staple line.

8. The method of claim 7, wherein the location mechanism includes a light, and using the location mechanism includes illuminating the light outside the bronchial tube.

9. The method of claim 7, wherein the location mechanism includes a magnet, and using the location mechanism includes the magnet magnetically engaging a target located within the bronchial tube adjacent to the reinforcement material.

10. The method of claim 7, wherein the reinforcement material comprises at least one of a mesh, a non-woven matrix, a film, a melt-blown non woven material, a felt material, a closed cell foam, an open-cell foam, a sponge, a braided suture, poliglecaprone, polyglactin, polydioxanone, collagen, oxidized cellulose, glycerol, glycolide, lactide, dioxanone, trimethylene carbonate, gut suture, polypropylene, polyethylene, polybutester fiber, stainless steel, nylon, polyester, silk, polyvinylidene difluoride, and polypropylene.

11. The method of claim 7, wherein the actuator includes a biologic foam.

12. The method of claim 7, wherein the reinforcement material irritates the bronchial tube.

13. The method of claim 7, wherein the location mechanism includes a sensor, and using the location mechanism includes the sensor sensing a magnet located within the bronchial tube.

14. The method of claim 13, wherein a grasper is used in positioning the reinforcement material within the bronchial tube, and the grasper has the magnet coupled thereto.

15. The method of claim 7, wherein the stapler also cuts the bronchial tube and the reinforcement material.

16. A surgical method, comprising:
transorally advancing a reinforcement material into a bronchial tube of a patient;

introducing a sealant into the bronchial tube and applying the sealant to the reinforcement material within the bronchial tube prior to the reinforcement material being fastened to the bronchial tube, the sealant transitioning from a first state to a second, harder state within the bronchial tube so as to secure the reinforcement material in a fixed position relative to the bronchial tube; and after the sealant is applied to the reinforcement material, fastening the reinforcement material to the bronchial tube with a fastener;

wherein advancing the reinforcement material includes advancing a distal end of a scoping device into the bronchial tube and introducing the reinforcement material into the bronchial tube through the scoping device;

wherein introducing the sealant includes introducing the sealant into the bronchial tube through the scoping device with the sealant in the first state; and wherein the scoping device has a balloon at the distal end thereof that is configured to move between an inflated configuration and an uninflated configuration, the balloon being in the inflated configuration during the introduction of the sealant into the bronchial tube through the scoping device and the balloon being in the uninflated configuration during the advancement of the distal end of the scoping device into the bronchial tube.

17. The method of claim 16, wherein the balloon is in the inflated configuration during the introduction of the reinforcement material into the bronchial tube through the scoping device.

18. The method of claim 16, wherein fastening the reinforcement material includes stapling the bronchial tube and the reinforcement material that has been introduced into the bronchial tube.

19. The method of claim 16, wherein the fastener is selected from the group consisting of staples, clips, sutures, and energy.

20. The method of claim 16, wherein the fastener includes a staple, and fastening the reinforcement material includes stapling the bronchial tube and reinforcement material using a stapler located outside of the bronchial tube.

* * * * *